Patent …

United States Patent [19]
Singh et al.

[11] 4,262,089
[45] Apr. 14, 1981

[54] THEOPHYLLINE ANTIGENS AND ANTIBODIES

[75] Inventors: Prithipal Singh, Santa Clara; Mae W. Hu, Sunnyvale, both of Calif.

[73] Assignee: Syva Company, Palo Alto, Calif.

[21] Appl. No.: 137,942

[22] Filed: Apr. 7, 1980

Related U.S. Application Data

[60] Division of Ser. No. 2,527, Jan. 11, 1979, which is a continuation of Ser. No. 787,829, Apr. 15, 1977, Pat. No. 4,156,081.

[51] Int. Cl.³ .......................... C12Q 1/66; C12N 9/96
[52] U.S. Cl. ........................................ 435/7; 435/810; 435/188; 424/12; 23/230 B
[58] Field of Search .................. 435/7, 188, 810, 177; 23/230 B; 424/12, 85; 260/112 R, 112 B, 121, 78 A; 544/271, 272; 528/49, 52

[56] References Cited
U.S. PATENT DOCUMENTS 4,067,774  1/1978  Rubenstein .............................. 435/7

OTHER PUBLICATIONS

Cook et al., "Theophylline Radio Immunoassay Synthesizing Antigen and Characterization of Antiserum", *Chem. Abstracts*, vol. 84, No. 21, (1976), pp. 8, 9, Abs. No. 144484t.

Nishikawa et al., "Competitive Nephelometric Immunoassay of Theophylline in Plasma, *Clin. Chim Acta*, vol. 91, No. 1, (1979), pp. 59–65.

Long, "Enzyme Immunoassay with Use of Centrifugal Analyzer of Phenytoin, Phenobarbital and Theophylline", *Clin Chem.*, vol. 24, No. 2, (1978), p. 391.

Schuurs et al., "Enzyme-Immunoassay", *Clin Chim Acta*, vol. 81, (1977), pp. 1–40.

*Primary Examiner*—Thomas G. Wiseman
*Attorney, Agent, or Firm*—Bertram I. Rowland

[57] ABSTRACT

Theophylline derivatives are provided for preparing reagents for use in competitive protein binding assays and for use as reagents in competitive protein binding assays. Theophylline is substituted at the 3 position and conjugated to antigens for production of antibodies which specifically recognize theophylline as distinct from structurally similar analogs such as caffeine. Enzyme conjugates are provided which find use for measuring the amount of theophylline in a sample suspected of containing theophylline. A method is provided employing the reagents for the determination of theophylline.

6 Claims, No Drawings

THEOPHYLLINE ANTIGENS AND ANTIBODIES

CROSS-REFERENCE TO RELATED APPLICATIONS

This is a divisional of application Ser. No. 002,527, filed Jan. 11, 1979, which was a continuation of application Ser. No. 787,829, filed Apr. 15, 1977, now U.S. Pat. No. 4,156,081, which issued on May 22, 1979.

BACKGROUND OF THE INVENTION

1. Field of the Invention

Theophylline (1,3-dimethylxanthine) is a drug commonly used in the treatment of asthma, hypertension and nephrotic edema. At elevated plasma levels, theophylline will sometimes produce nausea and serious toxic effects may occur at high plasma concentrations ranging from about 25–70 μg/ml. Serum theophylline shows considerable individual variation in patients, due to wide differences in the extent of metabolism and secretion as well as fluctuations during dosing intervals in the rate of absorption and distribution. With infants, the problems are further exacerbated, due to the infants low body fluid level.

In view of the serious side effects as a result of elevated serum theophylline levels, it is important that sensitive techniques be provided for monitoring theophylline levels. The technique should be rapid, accurate, and readily distinguish theophylline from its normal metabolites and widely prevalent analogs, such as xanthine and caffeine.

2. Description of the Prior Art

U.S. Pat. Nos. 3,690,834, 3,817,837, 3,850,752, and 3,766,162, and the references cited therein, describes a series of different immunoassays. The disclosure of U.S. Pat. No. 3,817,837 describing a homogeneous enzyme immunoassay is incorporated herein by reference. Synthesis of xanthine derivatives may be found in Advances in Heterocyclic Chemists 1966 Vol. VI, Lister et al, Rev. Pure & Applied Chem. (Australia). See also U.S. Pat. Nos. 2,517,410 and 2,673,848, as well as Holmes and Leonard, J. Org. Chem. 41 568(1976) and Cavalieri et al, J. Am. Chem. Soc. 76, 1119 (1954) for the preparation of xanthene derivatives. Rasmussen and Leonard, J. Am. Chem. Soc. 89 5439 (1967) discloses the use of pivaloyloxymethyl as a protecting group.

SUMMARY OF THE INVENTION

Theophylline derivatives are conjugated to antigens and enzymes. The antigenic theophylline conjugates are employed for the production of antibodies for specific recognition of theophylline. The enzymes conjugates are employed in competitive protein binding assays for the determination of theophylline, particularly in serum.

DESCRIPTION OF THE SPECIFIC EMBODIMENTS

The subject invention concerns 3-substituted-1-methylxanthines, which includes precursors, antigens for the preparation of antibodies to theophylline and enzyme conjugates which find use in competitive protein binding assays. The 3-substituent involves a short chain, usually, but not necessarily, involving a non-oxocarbonyl group, including the nitrogen and sulfur analogs thereof, joined to a poly(amino acid), which encompasses both natural and synthetic polypeptides, proteins and their combinations with prosthetic groups. The poly(amino acids) of particular interest are antigens and enzymes. The linking group may be a hydrocarbon group, that will normally have from 1 to 4 heteroatoms, which are oxygen, nitrogen, or sulfur, involved in the linking chain or bonded to carbon atoms in the chain. Usually, the chain will be of from about 1 to 10 atoms other than hydrogen, more usually from about 2 to 6 atoms other than hydrogen.

For the most part, the poly(amino acid) derivatives employed in this invention will have the following formula:

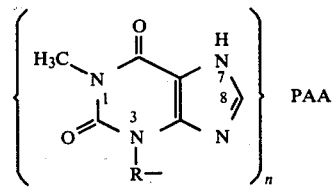

wherein: PAA refers to a poly(amino acid), particularly antigens and enzymes, wherein the antigens will normally be from about 5,000 to 10,000,000 molecular weight, more usually from about 10,000 to 500,000 molecular and preferably from about 25,000 to 300,000; while enzymes will normally be from about 10,000 to 600,000 molecular weight, more usually from about 10,000 to 300,000 molecular weight, and preferably from about 10,000 to 200,000 molecular weight;

n is the number of xanthine groups bonded to PAA and will be on the average at least 1 and up to the molecular weight of PAA divided by 1,500, more usually divided by 2,000; for antigens n will be generally on the average from 4 to 250, more usually from about 6 to 100; while for enzymes, n will generally be from about 1 to 30, more usually from about 2 to 20, and preferably from about 2 to 12; and R is a linking group which may be a bond, but is normally of from 1 to 12, more usually from 2 to 10 atoms other than hydrogen which are carbon, oxygen, nitrogen and sulfur, generally having from 0 to 1 sites of aliphatic unsaturation, usually ethylenic, and wherein oxygen will be present normally solely bonded to carbon i.e. ether or non-oxocarbonyl, nitrogen will be present as amido or tertiary-amino, and sulfur will be present as thioether or thiono; usually only oxygen and nitrogen will be present; R may be aliphatic, alicyclic, aromatic or combinations thereof, but will normally be aliphatic having not more than one site of aliphatic unsaturation e.g. ethylenic, and preferably saturated aliphatic.

The compounds prepared in accordance with this invention will be free or substantially free of xanthine substituted at the 7 and 8 positions. For the purpose of this invention, it is necessary that the products be solely 3-xanthine substituted.

For the most part, R groups will have the following formula:

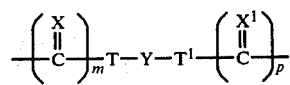

wherein:
- X and $X^1$ may be the same or different and are oxygen, imino(NH) or sulfur, particularly oxygen or imino;
- T and $T^1$ may be the same or different and may be a bond, a hydrocarbon radical of from 1 to 10 carbon atoms, more usually of from 1 to 4 carbon atoms, having a total of from 1 to 8 carbon atoms, more usually of from 1 to 6 carbon atoms, generally aliphatic, and preferably saturated aliphatic, particularly methylene or polymethylene, or $T^1$ may be hydrocarbylamino where the nitrogen is bonded to $(CX^1)$ wherein said hydrocarbyl group has the same limitation as for said hydrocarbon radical;
- Y is a bond, amido or oxy;
- m and p are integers of from 0 to 1, preferably p being 1 and m being 0, wherein CX is bonded to the xanthine and $CX^1$ is bonded to the poly(amino acid).

(By hydrocarbyl is intended an organic radical composed solely of hydrogen and carbon, which may be aliphatic, alicyclic, aromatic or combinations, saturated or unsaturated. For this invention, the hydrocarbyl groups will have not more than one site of unsaturation e.g. ethylenic)

Illustrative linking groups have the following formulae:

—CH$_2$CO—

—CH$_2$C(NH)—

—COCH$_2$CH$_2$CO—

—COCHCHCO—

—CH$_2$CONHCH$_2$CO—

—COCH$_2$N(CH$_3$)CH$_2$CO—

—CH$_2$CH$_2$C(NH)—

—COCH$_2$CH$_2$OCH$_2$CH$_2$CO—

—COCH$_2$OCH$_2$CO—

—CH$_2$CHCHCO—

The compounds which find use for conjugation to the poly(amino acid) will for the most part have the following formula:

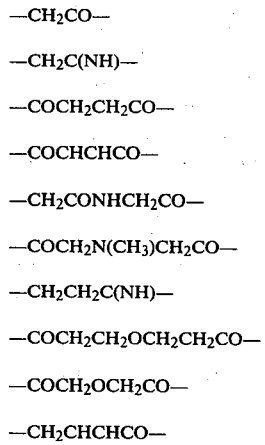

wherein:
- $R^1$ is a bond or linking group of from 1 to 12 atoms other than hydrogen, more usually of from 1 to 6 atoms other than hydrogen and preferably of from about 1 to 5 atoms other than hydrogen, which are carbon, oxygen, nitrogen and sulfur, wherein the characteristics set forth for carbon, oxygen, nitrogen and sulfur are as set forth for R;
- Z is oxocarbonyl (CHO), or non-oxo-carbonyl (includes the nitrogen-imido- and sulfur-thiono-analogs) carboxyl, carboxyester, wherein the ester group is nitrophenyl or N-succinimidyloxy, alkoxyimido, wherein the alkoxy group is of from 1 to 3 carbon atoms, isothiocyanate, or isocyanate.

The oxo group may be linked to available amino groups by reductive amination. The carboxylic acid groups and their nitrogen and sulfur analogs may be linked directly to available amino groups either by employing active esters, activating with carbodiimide or preparing a mixed anhydride with a chlorocarbonate ester e.g. alkoxycarbonyl of from 2 to 7 carbon atoms.

As indicated previously, of particular interest are compounds where the oxo-carbonyl group (other than keto) and the non-oxo-carbonyl group are bonded to an amino group, which is part of an antigenic polypeptide or protein. By bonding the carbonyl derivative of xanthine to the polypeptide or protein, antibodies can be formed to theophylline, which distinguish from caffeine in a competitive protein binding assay. A narrower class of proteins, which also can be used as antigens, but will not normally be used as such, are enzymes which are employed as the detector in an immunoassay system. As antigens, inactive enzymes can be used.

Polypeptides (referred to generally in the invention as poly(amino acid)) usually encompass from about 2 to 100 amino acid units (usually less than about 12,000 molecular weight). Larger polypeptides are arbitrarily called proteins. Proteins are usually composed of from 1 to 20 polypeptide chains called subunits, which are associated by covalent or noncovalent bonds. Subunits are normally of from about 100 to 300 amino acid groups (or 10,000 to 35,000 molecular weight). For the purposes of this invention, poly(amino acid) is intended to include individual polypeptide units and polypeptides which are subunits or polypeptide units in combination with other functional groups, such as prophyrins, as in haemoglobin or cytochrome oxidase.

The number of xanthine groups will vary depending upon whether the poly(amino acid) is an enzyme or antigen. The maximum number of groups will be limited by the effect of substitution on solubility, activity, and the like. For the formation of antibodies, a sufficient number of xanthine groups should be present, so as to provide a satisfactory harvest of antibodies to the theophylline (anti(theophylline)). Otherwise, the proportion of antibodies to theophylline as compared to antibodies to other compounds may be undesirably low.

The first group of protein materials or polypeptides which will be considered are the antigenic polypeptides. These may be joined to the carbonyl group of the theophylline analog through an amino group. The product can be used for the formation of antibodies to theophylline. The protein materials which may be used will vary widely, and will normally be from 5,000 to 10 million molecular weight, more usually 25,000 to 500,000 molecular weight.

Enzymes will normally be of molecular weights in the range of about 10,000 to 600,000, usually in the range of about 10,000 to 150,000, and more usually in the range of 12,000 to 80,000. Some enzymes will have a plurality of enzyme subunits. It is intended when speaking of enzyme molecular weights to refer to the entire enzyme. There will be on the average at least about one xanthine per enzyme, usually at least about two xanthines per enzyme, when the labeling is not limited to a specific amino group, and rarely more than 40 xanthines per enzyme, usually not more than 30 xanthines per enzyme. For example with lysozyme the average number of xanthine groups will be in the range of about 2 to 5. For glucose-6-phosphate dehydrogenase and malate dehydrogenase the average number will be in the range of 2 to 20, usually 2 to 12.

While the theophylline analog may be bonded through the non-oxo-carbonyl group to hydroxyl or mercapto groups, which are present in the proteins, for the most part the bonding will be to amino. Therefore, the compounds are described as amides (including nitrogen and thioanalogs e.g. amidine and thioamide. Also included within the non-oxo-carboxyl derivatives are urea, guanidine and thiourea.), although esters and thioesters may also be present. The aldehyde derivative will be bonded solely to amino to form alkylamine groups through reductive amination.

Amino acids present in proteins which have free amino groups for bonding to the carboxy modified xanthine includes lysine, N-terminal amino acids, etc. The hydroxyl and mercaptan containing amino acids include serine, cysteine, tyrosine and threonine.

Various protein and polypeptide types may be employed as the antigenic material. These types include albumins, enzymes, serum proteins, e.g., globulins, ocular lens proteins, lipoproteins, etc. illustrative proteins include bovine serum albumin, keyhole limpet hemocyanin, egg albumin, bovine gamma-globulin, etc. Small neutral polypeptides which are immunogenic such as gramicidins may also be employed. Various synthetic polypeptides may be employed, such as polymers of lysine, glutamic acid, phenyl-alanine, tyrosine, etc., either by themselves or in combination. Of particular interest is polylysine or a combination of lysine and glutamic acid. Any synthetic polypeptide must contain a sufficient number of free amino groups as, for example, provided by lysine.

The second group of protein molecules are the detectors. These are the enzymes to which the carbonyl modified xanthine may be conjugated. As indicated, the xanthine modified enzyme is useful for immunoassays. A description of the immunoassay technique will follow.

Various enzymes may be used such as peptidases, esterases, amidases, phosphorylases, carbohydrases, oxidases, e.g. dehydrogenase, reductases, and the like. Of particular interest are enzymes such as lysozyme, peroxidase, α-amylase, dehydrogenases, particularly malate dehydrogenase and glucose-6-phosphate dehydrogenase, alkaline phosphatase, β-glucuronidase, cellulase and phospholipase. In accordance with the I.U.B. Classification, the enzymes of interest are: 1. Oxidoreductases, particularly Group 1.1, and more particularly 1.1.1, and 1.11, more particularly, 1.11.1; and 3. Hydrolases, particularly 3.2, and more particularly 3.2.1.

The enzyme-bound-theophylline will for the most part have the following formula:

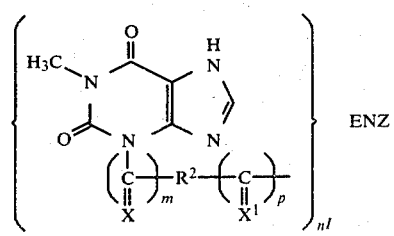

wherein:

ENZ is an enzyme, preferably an oxidoreductase or hydrolase, particularly oxidoreductases employing DPN or DPNP e.g. dehydrogenases, oxiodases and peroxidases or hydrolases, including esterases, e.g. phosphatases, lysozyme, and the like; the enzyme has at least 2% of its original activity, generally at least 10%, more usually at least 20% and preferably at least 30% of its original activity;

$n^1$ is an integer which on the average is in the range of 1 to the molecular weight of the enzyme divided by about 2,000, more usually in the range of about 1 to 30, preferably in the range of 1 to 20, and more preferably in the range of about 2 to 16;

$R^2$ is a linking group which may be a bond or a divalent organic radical of from 1 to 10 atoms other than hydrogen, which are carbon, oxygen, nitrogen and sulfur, particularly carbon, oxygen and nitrogen, and more particularly carbon and oxygen, the oxygen being present as oxy or non-oxocarbonyl, that is, bonded solely to carbon, and the nitrogen is amido or bonded solely to carbon is tertiary-amino, while sulfur is present as thiono; usually, $R^2$ is aliphatic having from 0 to 1 site of ethylenic unsaturation, preferably saturated, and will be of from 1 to 6 carbon atoms, more usually of from 1 to 4 carbon atoms, preferably methylene or polymethylene; and X, $X^1$, m have been defined previously.

The enzymes which are employed are preferably inhibited when the xanthine groups conjugated to the enzyme are bound to antibodies for the xanthine groups ie. anti(theophylline). The inhibition at saturation with anti(theophylline) should be at least 20% of the activity of the conjugated enzyme, usually at least 30% and preferably at least 40%, generally not more than 90%.

In forming the various amide products which find use in the subject invention, the carboxylic acid will normally be activated. This can be achieved in a number of ways. Two ways of particular interest are the reaction with a carbodiimide, usually a water soluble dialiphatic or dicycloaliphatic carbodiimide in an inert polar solvent, e.g. dimethylformamide, acetonitrile, THF, DMSO, and hexamethylphosphoramide. The reaction is carried out by bringing the various reagents together under mild conditions and allowing sufficient time for the reaction to occur.

A second method is to form a mixed anhydride employing an alkyl chloroformate, e.g. isobutyl chloroformate. The mixed anhydride is formed by combining the carboxy substituted xanthine, the alkyl chloroformate and tertiary amine. The temperature is normally below ambient temperature and a small amount of carbitol may be used.

At least a stoichiometric amount of the chloroformate is employed based on the xanthine derivative, and usually an excess, which usually does not exceed three times stoichiometric. The tertiary amine is present in at least equimolar amount to the chloroformate.

The mixture is then combined with the amino compound to be conjugated and the reaction allowed to proceed under mild conditions.

Also, esters of the carboxy modified xanthine can be employed which are operative in water for acylating amine functions. Illustrative hydroxylic groups are p-nitrophenyl and N-hydroxy succinimide which can be used to prepare the p-nitrophenyl and N-succinimidyloxy esters respectively. For the aldehyde conjugation, a reductive amination is carried out in a polar, usually aqueous medium, employing sodium cyanoborohydride as the reducing agent.

A novel and simple procedure is provided for the production of 1-methyl-3-substituted-xanthines free of other isomers. The starting material is 1-methylxanthine which is condensed with an approximately stoichiometric amount halomethyl pivalate (halo of atomic number 17 to 35, particularly chloro) under basic conditions in a polar anhydrous non-hydroxylic organic medium e.g. DMF, THF, DMSO, HMP, etc. Mild temperatures are employed 0° t 50° C., ambient temperatures being convenient. The base may be the nitrogen salt, sodium carbonate, tert-amine, etc. The reaction is allowed to proceed to completion and the mono-substituted-pivaloyloxymethyl derivative separated from any minor amounts of disubstituted material.

The 7-substituted product is isolated and combined with an alkyl ester of halosubstituted aliphatic carboxylic acid. The halo is of atomic number 17 to 53, preferably iodo, and is preferably co-substituted. The alkyl group of the alcohol portion is of from 1 to 6 carbon atoms, preferably 1 to 2 carbon atoms and the acid group is of from 2 to 7 carbon atoms. A basic anhydrous non-hydroxylic polar medium is employed, as described above, employing analogous reaction conditions.

After isolating the product, the ester groups are hydrolyzed under conventional conditions. Aqueous base may be employed at a temperature of from about 75° to 100° C. Upon acidification of the solution the desired 1-methyl-3-carboxylalkylxanthine may be isolated.

The antibodies which are prepared in response to the conjugated antigens of this invention have strong specific binding to the parent drug, the conjugated antigen, the compound or derivative thereof used to conjugate to the antigen, and the enzyme conjugate.

The assay will be able to detect theophylline in the concentration range 0 to 100 µg/ml and should be able to distinguish between no theophylline and 5 µg/ml, preferably 2.5 µg/ml. Normally, the sample of interest will be serum, although other sample sources may be employed.

The assay will generally be carried out by combining in an aqueous buffered medium, generally at a pH in the range of 5 to 10, more usually 6 to 9, the sample to be assayed, enzyme-bound-theophylline and anti(theophylline). Besides water up to 20 volume percent of polar organic solvents may be included in the assay medium, e.g. alkanols, ethers, amides, etc.

The amounts of the reagents will vary depending upon the enzyme activity of the enzyme-bound-theophylline, the degree of inhibition resulting from binding of anti(theophylline) to the enzyme-bound-theophylline, the manner of measurement, the sensitivity of the reagent combination to variations in the concentration of theophylline, the binding constant of the anti(theophylline) and the like. the primary concern is that a reasonable spread of measured values can be obtained over the theophylline range of interest. When measuring changes in optical density due to changes in the light absorption of the assay medium as a result of an enzymatic transformation, over a theophylline concentration range of about 0 to 50 µg/ml, the measured change in absorption should be at least about 0.25ΔOD, preferably at least 0.5ΔOD.

Usually, the mole ratio of anti(theophylline) based on binding sites to theophylline in enzyme-bound-theophylline will be about 0.01-100:1. The concentration of enzyme-bound-theophylline will generally be in the range of about $10^{-5}$ to $10^{-10}$.

Included in the assay medium will be the enzyme substrates. Usually, one of the substrates will be transformed to a product which has a distinctive absorption in the ultraviolet or visible region. Conveniently enzymes can be employed which transform NAD or NADP to NADH or NADPH and the formation of NADH or NADPH followed spectrophotometrically. By taking two readings at a particular wavelength over a predeterminted time period, a rate value can be obtained which relates to the enzymatic activity. By employing the same protocol with an unknown sample as employed with samples spiked with known concentrations of theophylline, the result obtained can be translated into a theophylline concentration.

Temperatures for the assay will generally be in the range of about 10°-50° C., usually in the range 25°-40° C.

EXPERIMENTAL

The following examples are offered by way of illustration and not by way of limitation. (All percents not otherwise indicated are by weight, except for mixtures of liquids which are by volume. All temperatures not otherwise indicated are centigrade. Abbreviations include DMF for N,N-dimethylformamide; TLC, thin layer chromotography; ECDI, 1-ethyl-3-(dimethylaminopropyl) carbodiimide hydrochloride; THF, tetrahydrofuran.

EXAMPLE 1

Preparation of 1-methyl-7-pivaloyloxymethyl xanthine

To a mixture of 1-methylxanthine (844 mg, 5.08 mmoles) and sodium carbonate (538 mg, 5.08 mmoles) is 20 ml of dry DMF under nitrogen was slowly added over a period of 1 hour a solution of chloromethylpivalate (828 µl, 5.59 mmole) in 6 ml DMF at room temperature and the reaction mixture stirred overnight. The mixture was filtered, the filtrate evaporated to dryness and the residue triturated with 50 ml of 10 vol. %. EtOH/CHCl$_3$. The solids obtained were starting material and the organic phase was chromatographed (10 vol. % EtOH/CHCl$_3$) on silica gel plates. Two products were observed by eluting with 125 ml of 10 vol. % EtOH/CHCl$_3$ and the band R$_f$, 0.48 obtained as 365 mg of the desired product. The other band proved to be the 3,7-disubstituted material.

EXAMPLE 2

Preparation of 1-methyl-3-(carboethoxypropyl)-7-(pivaloyloxymethyl)xanthine

A mixture of 1-methyl-7-(pivaloyloxymethyl)xanthine (350 mg, 1.25 mmes) sodium carbonate (265 mg, 2.50 mmoles) and ethyl 4-iodobutyrate (384 µl, 2.50 mmole) in 5.8 ml dry DMF was stirred under nitrogen at room temperature for 18 hours. Water was added and the reaction mixture extracted with chloroform. After drying, the extracts were stripped to leave a yellow oil which goes to chromatographed on four thick silica gel plates with 10% EtOH/CHCl$_3$. The band was scraped off and eluted with 100 ml of 25% EtOH/CHCl$_3$ to yield 609 mg of the desired product as an oil.

EXAMPLE 3

Preparation of 1-methyl-3-(3'-carboxypropyl)xanthine

An oily suspension of 1-methyl-3(carboethoxypropyl)-7-(pivaloyloxymethyl)xanthine (508 mg) in 2N NaOH (36.2 ml) was heated under nitrogen at 95°–100° for 2 hrs. The oil dissolved and the reaction was shown to be complete by TLC. After cooling the reaction mixture, it was acidified to pH 2-3 with 15 ml 12% hydrochloric acid and the solution extracted with 3×5 ml chloroform to remove the pivalic acid. After washing the chloroform extracts with 5 ml 0.5N HCl, aqueous solutions were combined and stripped to dryness and the residue dried in vacuo at room temperature. The crude product was dissolved in about 22 ml hot water, decolorized and concentrated to 15 ml, at which time 159 mg of a crystalline product was obtained upon cooling. m.p. 220°–221°.

EXAMPLE 4

Conjugation of 1-methyl-3-(3'-carboxypropyl)xanthine with bovine gamma globulin

To a clear solution of 1-methyl-3-(3-carboxypropyl)xanthine (45 mg, 0.178 mmole) in 1.5 ml DMF was added N-hydroxysuccinimide (20.5 mg, 178 mmole) and EDCI (39.1 mg, 0.20 mmole) at 0° under nitrogen. After stirring the solution at 5° for 18 hours, the reaction mixture was added to a solution of bovine gamma globulin (550 mg) in a mixture of 27 ml carbonate buffer (ph 9, 0.05 M) and DMF at 0° and the mixture maintained at this temperature for a period of 1.5 hours, while maintaining the pH at 8.5–9.0 using 1N NaOH. After stirring the mixture overnight at 5°, the product was dialyzed against 10×4 l. water and 3×4 l. ammonium hydroxide. Lyophilization of the conjugate yielded 470 mg of protein. Employing a spectrophotometric technique, the hapten number was determined to be 15.

EXAMPLE 5

Preparation of 3-(2'-cyanoethyl)-1-methylxanthine

Into a reaction flask was introduced 7-pivaloyloxymethyl-1-methylxanthine (100 mg) dissolved in 1.42 ml DMF, 44.17 mg sodium carbonate and 47 µl acrylonitrile. After heating at 100° for 16 hours, the mixture was poured into water and the aqueous mixture extracted with chloroform. The chloroform extracts were dried and evaporated and the oily residue chromatographed twice on silica gel plates, and the band eluted with 75 ml of 25% ethanol/chloroform (v/v) to give 109 mg of an oily product which solidified on standing. mp 118–120.

The above nitrile (109 mg) was suspended in 0.35 ml 1N sodium hydroxide and 0.35 ml of THF added. The mixture was stirred at room temperature for 3.5 hours, followed by the addition of 0.2 ml of 1N sodium hydroxide and stirring continued for an additional 0.5 hour. The mixture was then poured into about 2 ml water, the aqueous solution acidified and extracted exhaustively with chloroform. The chloroform extracts were washed with 8% sodium bicarbonate, followed by drying and evaporation to dryness. The residue was chromotographed on two silica gel plates (10% EtOH/HCCl$_3$) and eluted with 125 ml 25% EtOH/HCCl$_3$. Evaporation to dryness yield 50 mg of the desired product.

The subject nitrile can be readily modified to the imidoester and used for conjugation to amino groups present in poly(amino acids) to provide amidine linkages.

EXAMPLE 6

Conjugation of 3-carboxypropyl-1-methylxanthine to glucose-6-phosphate dehydrogenase A lyophilized powder of G6PDH was dissolved in 0.055M tris-HCl, pH 8.1, to a protein concentration of about 2–3 mg/ml. The mixture was allowed to stand overnight at 4°.

Into a reaction flask was introduced 3-carboxypropyl-1-methylxanthine (36 mg, 0.14 mmoles), 16.4 mg of N-hydroxy succinimide, 31.4 mg of ECDI and 400 µl of DMF and the mixture stirred overnight at 4°.

To 5 ml of the above G6PDH solution is added 50 mg glucose-6-phosphate disodium salt, 100 mg of NADH and 1.5 ml of carbitol and the pH adjusted to about 8.5–9 with 2N sodium hydroxide. Almost the entire 400 µl of the ester prepared above is added to the stirring enzyme solution in 10 µl increments over a 2 hour period while maintaining the solution at 4°. During the reaction the pH drops to 7.5–8. The resulting conjugate is then dialyzed at 4° against 0.055M tris HCl, pH 8.1, containing as preservatives 0.5% sodium azide and 0.005% thimerosal.

In order to demonstrate the effectiveness of the subject compositions in an assay for theophylline, a number of assays were carried out.

In carrying out the assay, a Gilford 300N Microsample Spectrophotometer is employed, with a Thermocuvette with a flow cell. All readings are made at 340 nm. The following solutions are prepared as reagents for use in the assay:

TABLE I

| Buffer: | 0.055M tris-HCl, pH 8.1 (RT) |
| --- | --- |
| | 0.05% sodium azide |
| | 0.005% Thimerosal |
| Enzyme conjugate: | Buffer |
| | 0.9% NaCl |
| | 1.0% RSA,* pH 8.1 (RT) |
| | sufficient enzyme conjugate (Ex. 1) |
| | to give a rate of ΔOD in the range of 350–500 |
| | in the assay medium. |
| Assay Buffer: | Buffer |
| | 0.5% NaCl |
| | 0.01% (v/v) Triton X-100, pH 8.1 (RT) |
| Antibody Reagent: | Buffer |
| | 1.0% RSA |
| | 1-methylxanthine 1.67µg/ml |
| | G6P(Na) 0.066M |
| | NAD 0.04M |
| | pH 5 (RT) |
| | antitheophylline optimized for assay |

All % unless otherwise indicated are w/v (g/ml)
*RSA-rabbit serum albumin

The protocol employed for carrying out an assay is as follows. 50 µl of the sample is drawn up into a diluter and dispensed with 250 µl of the assay buffer into a 1 ml Croan cup. A 50 µl aliquot of the diluted sample is drawn up and dispensed with a 250 µl portion of assay buffer into a second Croan cup. Into the second Croan cup is introduced 50 µl of the antibody reagent with 250 µl of the assay buffer, followed by the addition of 50 µl of the enzyme reagent and 250 µl of the assay buffer. Immediately after the enzyme addition, the entire sample is aspirated into the flow cell. After 15 sec. a first reading is taken, followed by a second reading after a thirty second interval. Thre results are reported as the difference in absorbance ×2.667.

The following table indicates the results obtained with a number of samples having known amounts of theophylline.

TABLE II

| Theophylline Conc. in Sample μg/ml | ΔODx 2.667 |
|---|---|
| 0 | 163 |
| 2.5 | 201 |
| 5 | 221 |
| 10 | 244 |
| 20 | 267 |
| 40 | 292 |

By graphing the above results on semilog paper, one can then determine the concentration of theophylline in a sample suspected of containing theophylline by comparing the ΔOD obtained with the unknown sample with the concentration-ΔOD plot obtained with the above results.

It is found that the cross-reactivity due to 1-methylxanthine can be effectively damped by the addition of a small amount of 1-methylxanthine to the antibody reagent, generally a sufficient amount to provide from about 1 to 20, preferably 2 to 15 μg/ml in the assay medium. In this manner, false positives can be avoided, where 1-methylxanthine is present to any extent in the serum sample to be assayed.

A cross-reactivity study was made with a wide variety of similarily structured compounds. The subject assay must be able to distinguish between ubiquitous compounds of analogous structures to theophylline, such as caffeine and its metabolites, in order to insure an accurate result. Compounds studied for cross-reactivity were caffeine, 1,3-dimethyluric acid, theobromine, 1-methylxanthine and 3-methylxanthine. When samples were spiked with 100 μg/ml of these compounds, with the one exception of 1-methylxanthine, the observed value was below the value obtained with 2.5 μg/ml of theophylline. The one exception was 1-methylxanthine where 100 μg/ml of 1-methylxanthine is equivalent to 5–10 μg/ml concentration of theophylline. However, as indicated above, when a small amount of 1-methylxanthine is employed in the assay medium, substantially no effect is seen by the addition of further 1-methylxanthine.

It is evident from the above results, that the subject invention provides a sensitive assay for measuring theophylline in physiological fluids, particularly serum. The assay protocol provides for distinguishing theophylline at extremely low concentrations from compounds having extremely similar structures. Furthermore, the protocol is simple, fast, and is readily carried out on a conventional spectrophotometer.

Although the foregoing invention has been described is some detail by way of illustration and example for purposes of clarity of understanding, it will be obvious that certain changes and modifications may be practiced within the scope of the appended claims.

What is claimed is:

1. A method for the determination of theophylline in a sample suspected of containing theophylline, which comprises:
   bringing together in a aqueous medium;
   (1) said sample;
   (2) enzyme bound theophylline; and
   (3) antitheophylline produced from theophylline linked to an antigen at its 3 position.
   wherein said antitheophylline is at a concentration resulting in substantial reduction in enzymatic activity of said enzyme bound theophylline in the absence of theophylline; and analyzing in said medium for the effect of said sample on the enzymatic activity of said enzyme bound theophylline.

2. A method according to claim 1 wherein said medium contains from about 1 to 20 μg/ml of 1-methylxanthine.

3. A method according to claim 1, wherein said enzyme is glucose-6-phosphate dehydrogenase.

4. A method according to claim 3, wherein included in said medium is from 1 to 20 μg/ml of 1-methylxanthine.

5. A reagent kit for use in a method according to claim 1, comprising enzyme bound theophylline and antitheophylline, wherein said antitheophylline is produced from theophylline linked to an antigen at its 3 position is at a concentration resulting in substantial reduction in enzymatic activity of said enzyme bound theophylline in the absence of theophylline.

6. A kit according to claim 5, including with said antibody an amount of 1-methyxanthine sufficient to provide from about 1 to 20 μg ml in said medium.

* * * * *